United States Patent
Reszka et al.

(10) Patent No.: US 6,479,033 B1
(45) Date of Patent: *Nov. 12, 2002

(54) ANTITUMOR CYSTOSTATIC AND CONTRAST AGENT

(75) Inventors: Regina Reszka, Schwanebeck (DE); Uwe Pohlen, Berlin (DE); Detlef Stiller, Magdeburg (DE); Gerd Berger, Berlin (DE); Matthias Lippmann, Berlin (DE)

(73) Assignee: Max Delbrück Zentrum für Molekulare Medizin, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/906,603

(22) Filed: Jun. 16, 1997

Related U.S. Application Data

(63) Continuation of application No. PCT/DE94/01524, filed on Dec. 16, 1994.

(51) Int. Cl.[7] ............... A61B 5/055; A61K 49/00; A61K 9/127
(52) U.S. Cl. ............... 424/9.32; 424/9.3; 424/9.36; 424/9.4; 424/9.45; 424/450
(58) Field of Search ............... 424/9.32, 9.3, 424/9.321, 9.322, 9.35, 9.36, 9.364, 9.365, 9.4, 9.43, 9.45, 450, 489, 492, 493, 498, 499, 649

(56) References Cited

U.S. PATENT DOCUMENTS

| 5,542,935 A | * | 8/1996 | Unger et al. ............... 604/190 |
| 5,620,703 A |   | 4/1997 | Reszka et al. ............... 424/450 |
| 6,207,133 B1 | * | 3/2001 | Reszka et al. ........... 424/9.321 |

FOREIGN PATENT DOCUMENTS

| DE | 4341478 A1 | * | 6/1995 | .......... A61K/31/28 |
| WO | WO 92/17214 | * | 10/1992 | .......... A61K/49/00 |

* cited by examiner

*Primary Examiner*—Michael G. Hartley
(74) *Attorney, Agent, or Firm*—Goodwin Procter LLP

(57) ABSTRACT

The invention concerns a composition for the treatment of tumors, of (i) at least one cytostatic drug component which is unencapsulated or is encapsulated in a PEG-, immuno-, or immuno/PEG liposome, (ii) at least one of lyophilized starch particles, degradable starch particles, and gelatine, in combination with (iii) a contrasting agent containing at least one of iodine, gadolinium, and magnetite.

22 Claims, 12 Drawing Sheets

RESULTS

| DOSAGE FORM | TUMOR GROWTH BY FACTOR (7 DAYS AFTER TREATMENT) | ACCUMALATION OF CONTRAST AGENT IN LIVER |
|---|---|---|
| CONTROL | 3.65 ± 2.45 | UNCHANGED |
| SPHEREX | 2.38 ± 1.35 | → 6% |
| GELFOAM | 3.93 ± 1.66 | UNCHANGED |
| CARBOPLATIN | 1.45 ± 0.96 | → 7% |
| CARBOPLATIN/SPHEREX | 1.15 ± 0.24 | → 19% |
| CARBOPLATIN/GELFOAM | 0.85 ± 0.08 | → 11% |

FIG. 1

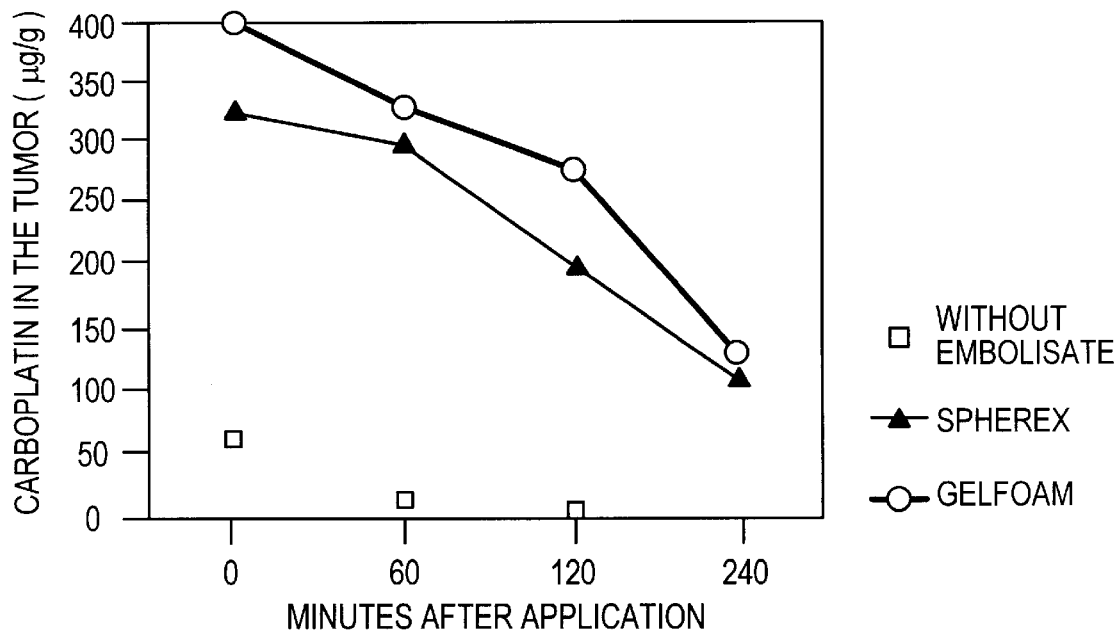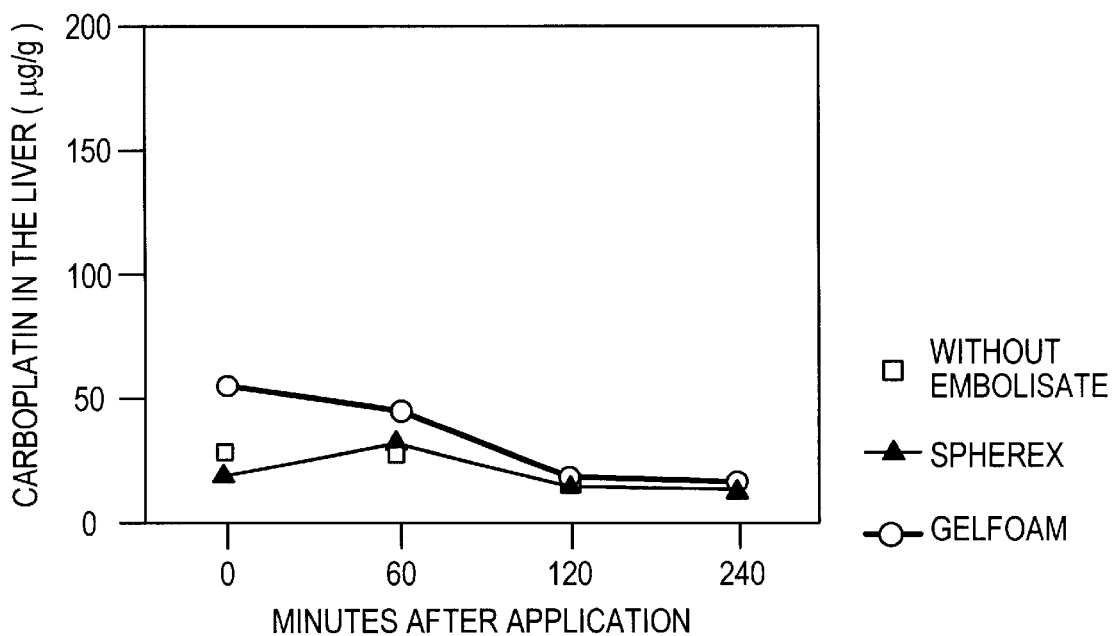
FIG. 8

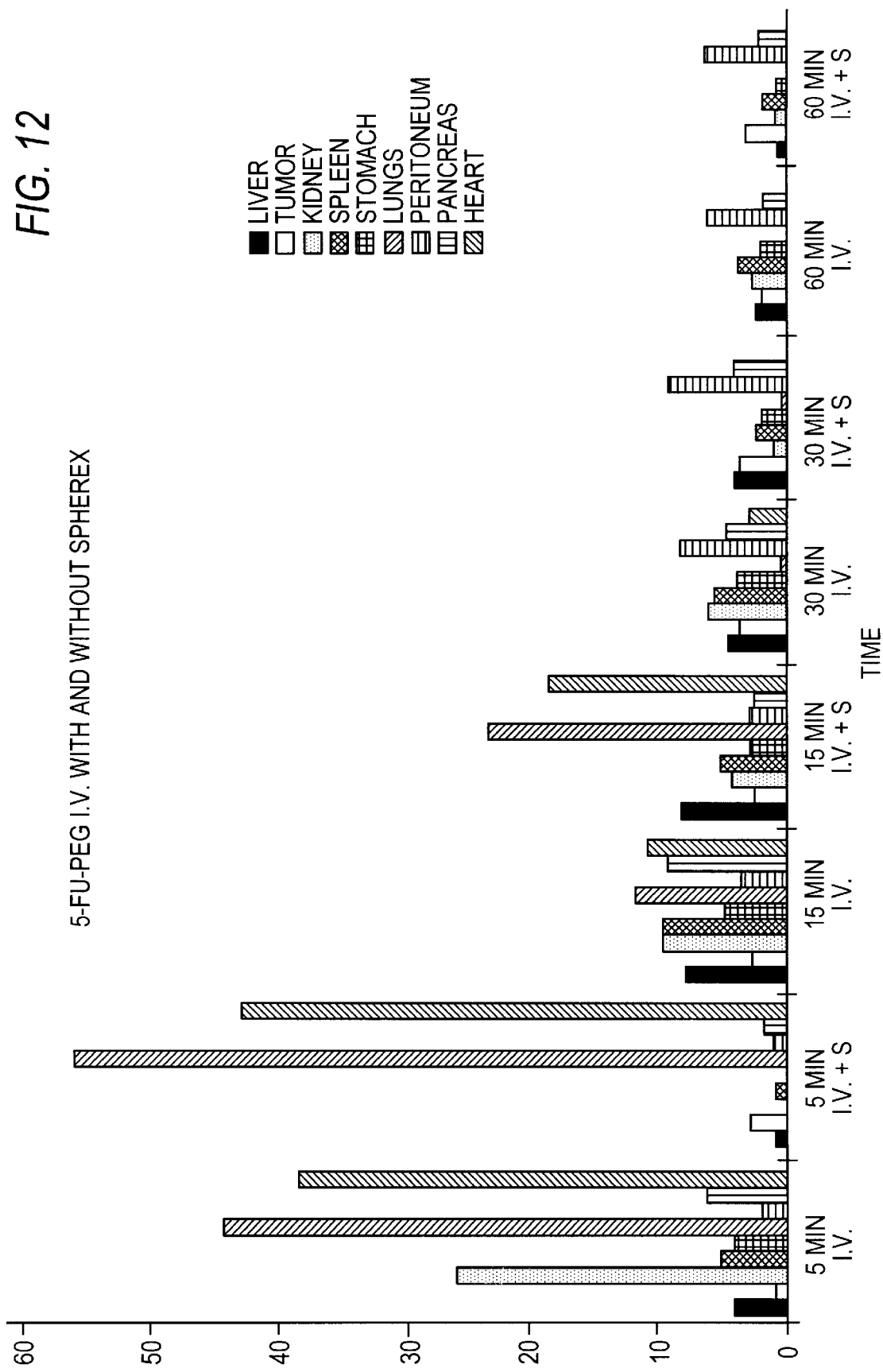

ANTITUMOR CYSTOSTATIC AND CONTRAST AGENT

This is a continuation of PCT/DE94/01524, filed on Dec. 16, 1994.

FIELD OF INVENTION

The invention relates to a composition for the treatment of tumors, its production and its use and, in particular, for the treatment of non-resectable primary and metastasized liver tumors.

BACKGROUND

In anti-tumor therapy of non-resectable liver tumors, the regional administration of cytostatic drugs, in conjunction with flow-retarding substances to increase the local concentration of the cytostatic drugs at the tumor, has proven to be meaningful. In particular, as has been described by Link as well as by Collins, an endeavor should be made to increase the concentration of the cytostatic drug at the tumor site in accordance with the dose-effect relationship and, at the same time, to preserve the surrounding liver parenchyma. It is the objective here to achieve the above-described effects at the tumor and, at the same time, to minimize systemic side effects. This principle has already, been realized many years ago in chemo-embolization.

Various problems arise when this form of therapy is employed. Until now, the complete embolization could be portrayed only indirectly by means of various methods. For this purpose, an iodine-containing contrasting agent was injected for the application of the chemoembolism until there is a retrograde flow of contrasting agent; a further method makes use of the addition of lipoidol, which shows the hepatofugal or hepatopedal flow as small iodine-containing containing fat bubbles.

The indirect method has the disadvantage that a retrograde runoff of the mixture of cytostatic drug and embolisate is not always noticed, as a result of which dangerous complications may arise (gastrointestinal necroses). There are therefore limitations to the applicability in facilities with simple X-ray equipment.

Several antitumor therapy preparations are known. In U.S. Pat. No. 5,620,703 and German patent No. 4,341,478, a preparation is described, which can be used particularly for the therapy of non-resectable, primary and secondary liver tumors. This preparation contains lyophilized starch particles, which are combined with one or more cytostatic drugs and are dissolved in iodine-, gadolinium- or magnetite-containing contrasting agents. Carboplatin is a suitably cytostatic drug for this preparation.

A high concentration of the cytostatic drug used is attained with the preparation aforementioned in the tumor to be treated. It is, however a disadvantage that the residence time in the tumor is only about 4–6 hours. This is generally not adequate for a successful therapy.

SUMMARY OF THE INVENTION

It is an object of the invention to avoid the disadvantages that arise during the chemoembolization of tumors and to develop an optimum embolisate, which not only shows the effect brought about the respective vascular structure of the tumor, but can also be portrayed directly and reliably in tumor monitoring.

It is an other object of the invention to build up a drug targeting system for fighting cancer by means of suitable carrier systems to accumulate cytostatic drugs in the tumor and to increase the residence time in the tumor clearly. At the same time, toxic side effects on the remaining organs shall be decreased.

The composition of the present invention contains lyophilized starch particles in combination with cytostatic drugs, dissolved in iodine-, gadolinium- or magnetite-containing contrasting agents.

The lyophilized starch particles are an important component of the composition of the present invention. Particles, 40–90 $\mu$m in size, more suitably of from 60 $\mu$m to 90 $\mu$m; they are suitably dissolved in physiological salt solution up to a concentration of from 5 mg/ml to 70 mg/ml and then lyophilized in a manner known per se. A gelatine, particularly an absorbable gelatine powder is suitable.

All known cytostatic drugs can be used. For example, carboplatin, which is mixed, also in lyophilized form, with the lyophilized starch. Suitable cytostatic drugs also include 5-fluorouracyl, and 5-fluorouridine.

Liquid, iodine-containing compounds, suitably iodo-or polyiodophenyl derivatives, are used as iodine-containing contrast agents. Suitable materials include Iopromide, Ioxitalamate, Ioxaglate, Iopamidol, Iohexol, Iotralon, Metrizamide or Ultravist. At the same time, the contrasting agent serves as solvent for the mixture of the lyophilisates.

Either gadolinium- or magnetite-containing contrasting agents are used for the magnetic resonance tomography (MRT). Suitably from 30 mg to 90 mg lyophilized or degradable starch particles are mixed in the required. amounts of cytostatic drug and subsequently dissolved in from 3 ml to 6 ml of contrasting agent. It is also possible to dissolve the given amount of lyophilized starch particles first in the contrast agent and, after that, add the therapeutically necessary amount, such as from 5 mg to too mg of the cytostatic drug.

A conventional, commercial embolisate sold by Kabi Pharmazia under the trade name Spherex is suitably the starting material for the preparation of lyophilized starch particles. This product is dialyzed in the dialysis tube against doubly distilled sterile water for 36 hours with a threefold exchange of water. After that, the material is removed from the dialysis tube with a sterile pipette and frozen in a sterile plastic vessel at –70° C. The cold vessel is brought into the freezedryer and dried for 24 hours under a high vacuum.

The following describes the use of the preparation and its effects. The requirements, which have to be met by an embolisate for tumor therapy, depend on the vascular structure of the tumor, that is, the particles should be of a suitable size to reach the tumor together with the cytostatic drug over an embolization of, as far as possible, peripheral portions of the vascular bed of the tumor. The optimum particle size for this lies between 40 and 90 $\mu$m. A deviation in size from that given above in the direction of larger particles brings about a stasis in the supplying tumor vessels, so that the cytostatic drug cannot reach the tumor in an optimally high concentration. This is due to a peripheral blood inflow over the opening of an arteriovenous shunt and the therewith associated dilution effect for the cytostatic drug. An even smaller particle size can lead to multiple systemic embolizations, such as lung embolisms.

The starch particles, lyophilized pursuant to the invention, exhibit embolization behavior lasting for 20 to 60 minutes. An interval therapy with this briefly effective embolisate has proven to be advantageous in comparison to embolisates, which are effective for a longer time. During the desarterilization (Bengmark. etc.), there is an angioproliferative effect, which sets in rapidly, so that there is neovascularization of the tumor within 48 hours and a renewed attempt at therapy is thus made difficult. Similar effects are also seen when a long-acting embolisates are used with thrombosis of the supplying tumor vessels and connection of the tumor vessels, for example, to the diaphragm, the greater omentum, etc., which limit further therapy.

The new preparation and its use enable without the help of indirect methods, using X-ray fluoroscopy, a sufficient embolization being portrayed directly, the tumor with its blood vessels being imaged as a still picture; using gadolinium- or magnetite-containing contrast drugs in combination with flow-coded measurement sequences, and the embolization can also be portrayed with the help of magnetic resonance. tomography; the attainable concentration of cytostatic drugs in the tumor tissue is considerably increased (by up to a factor of 20) in comparison to other forms of administration; and the application is simplified while, at the same time, the safety is increased (retrograde faulty perfusion is avoided).

Accordingly, with this form of therapy, a broad application can be made accessible, also outside of special therapy centers.

BRIEF DESCRIPTION OF THE DRAWING

The invention is described in greater detail with reference to the drawing wherein FIGS. 1 to 3 show the pharmacokinetics in the tumor and the liver;

FIG. 8 shows concentration in the tumor and liver;

FIG. 12 shows administration with and without Spherex.

DETAILED DESCRIPTION

The invention is explained herein below in greater detail also by reference to an Examples.

A port system is implanted in the A. gastroduodenalis of male Chinchilla rabbits with a VX-"- tumor, 2 cm in diameter, implanted in the liver. According to a fixed schedule, either the therapeutic preparation of the present invention or a mixture of equal doses of the conventional, commercial form was administered to the animals through this system. The preparation in each case contained 60 mg of Spherex and 50 mg of carboplatin with 5 ml of a 300 mg/ml iodine-containing contrast agent (Ultravist 300, Schering). At fixed times of 15, 30, 60, 120, and 240 minutes, the animals were sacrificed and the concentration of cytostatic drugs was determined analytically in different tissues (tumor, liver, spleen, kidneys, serum) using atomic absorption spectroscopy. The concentration of the cytostatic drug had increased by a factor of up to 20 in the tumor tissue.

By directly using X-ray fluoroscopy, it was possible to observe the administration of the newly developed composition without any problems. The gradual saturation of the vascular bed of the tumor, from the periphery up to the vascular trunk, is portrayed by still pictures over the whole phase of the embolization and could be reconstructed during the entire duration of the vascular occlusion as a still picture. It was likewise possible to document the onset of reperfusion.

Figure 2:
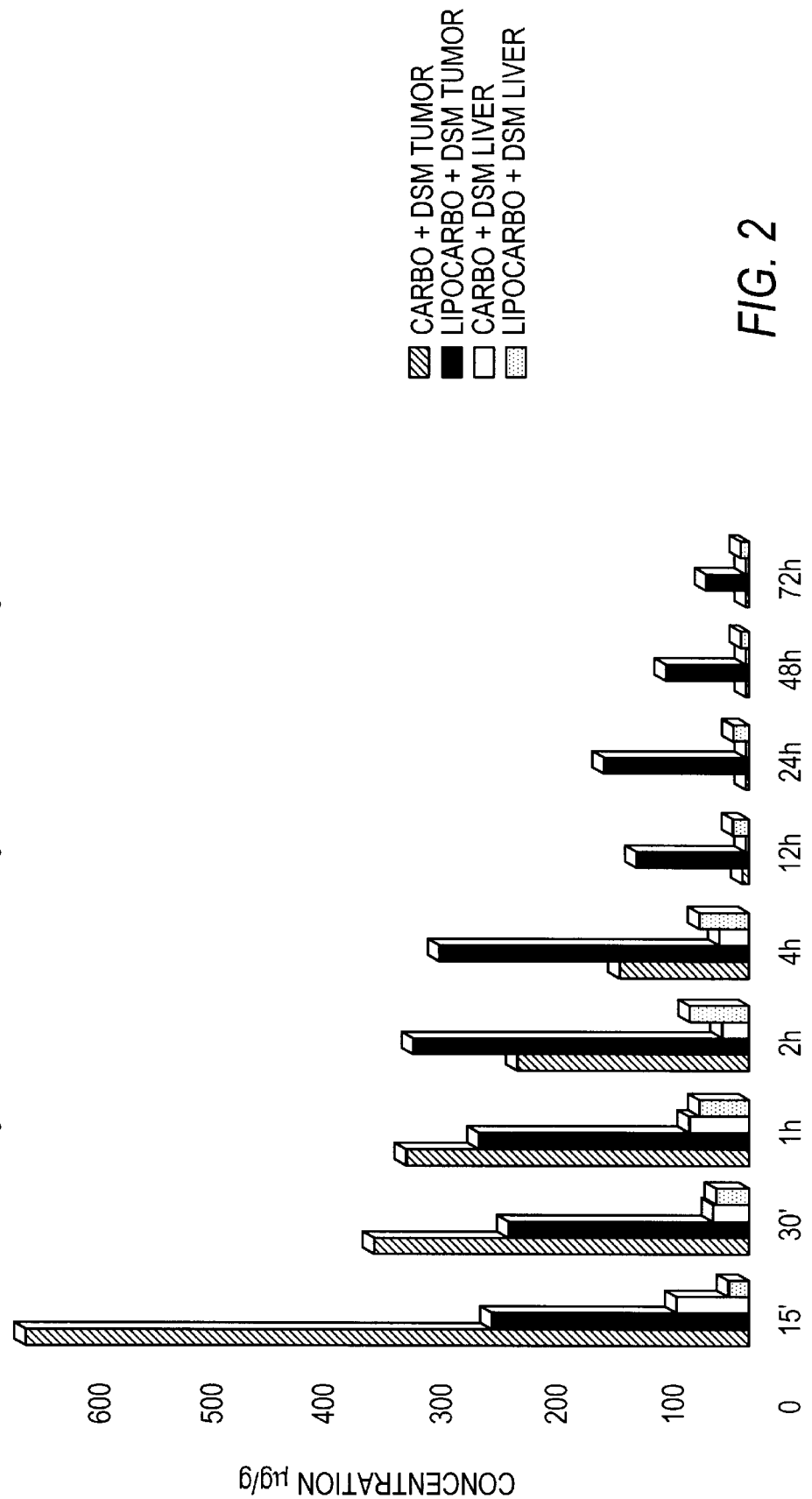
Figure 3:
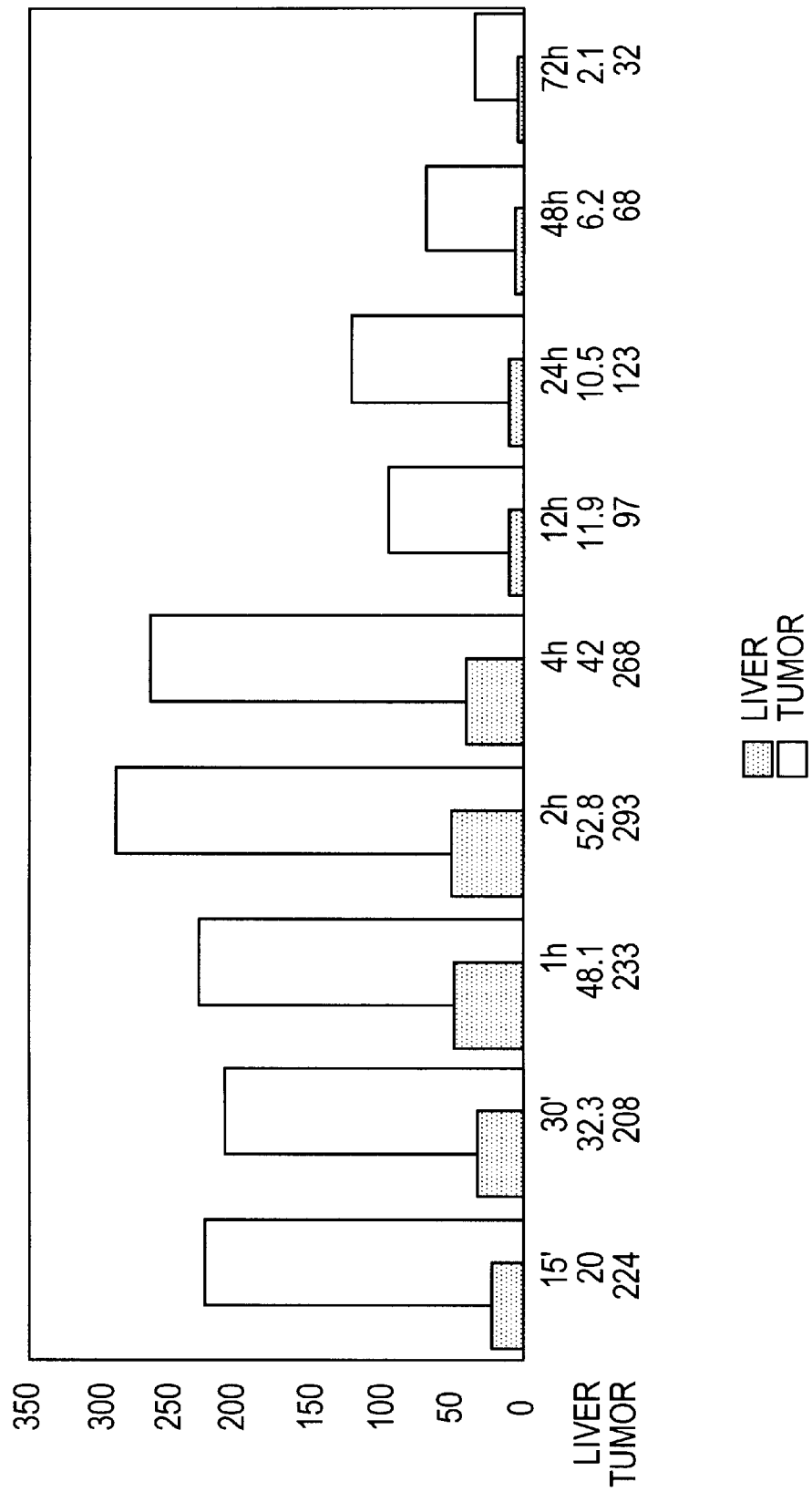
Figure 4:
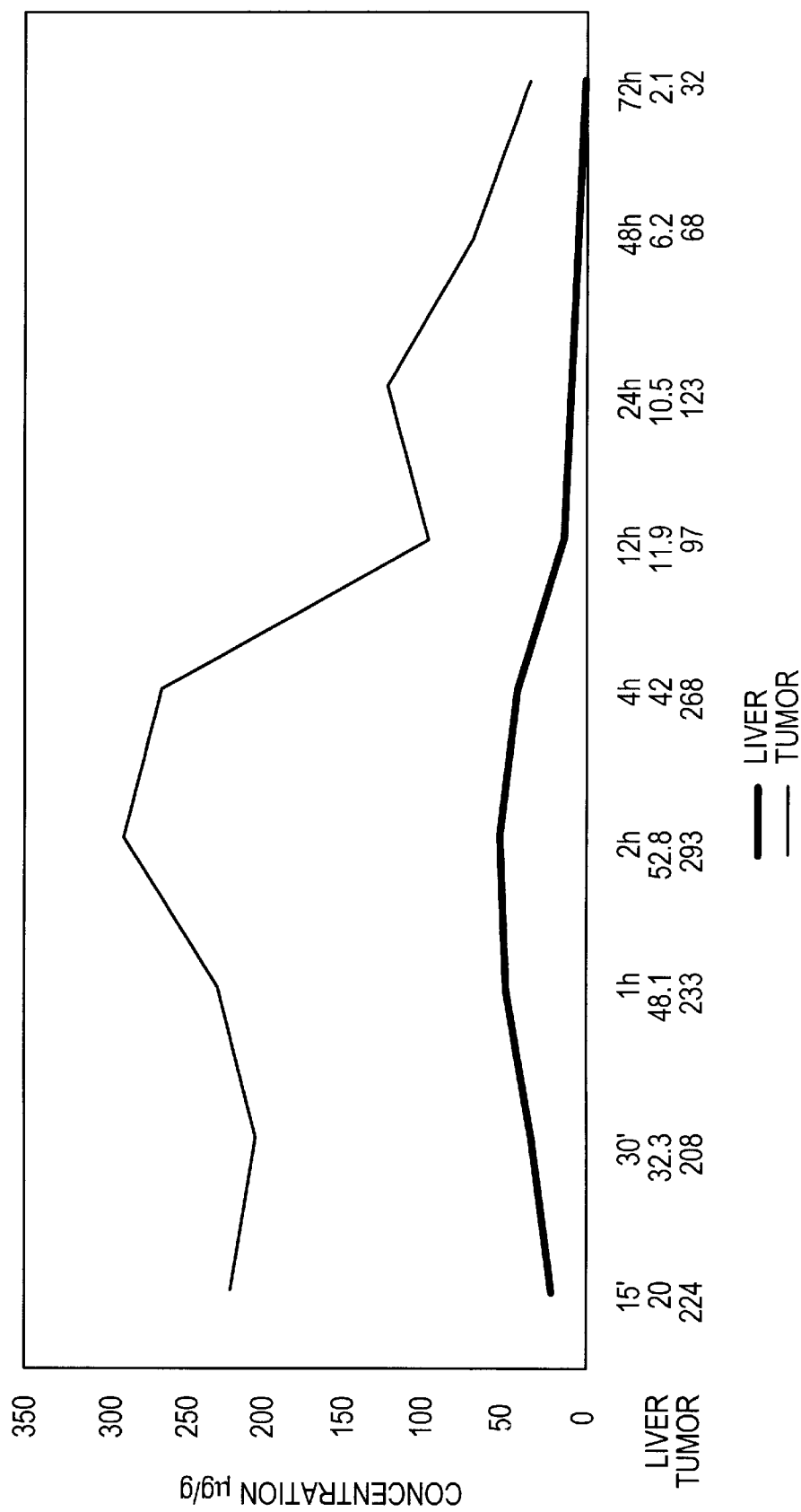
FIG. 4 shows the organ concentration.
Figure 5:
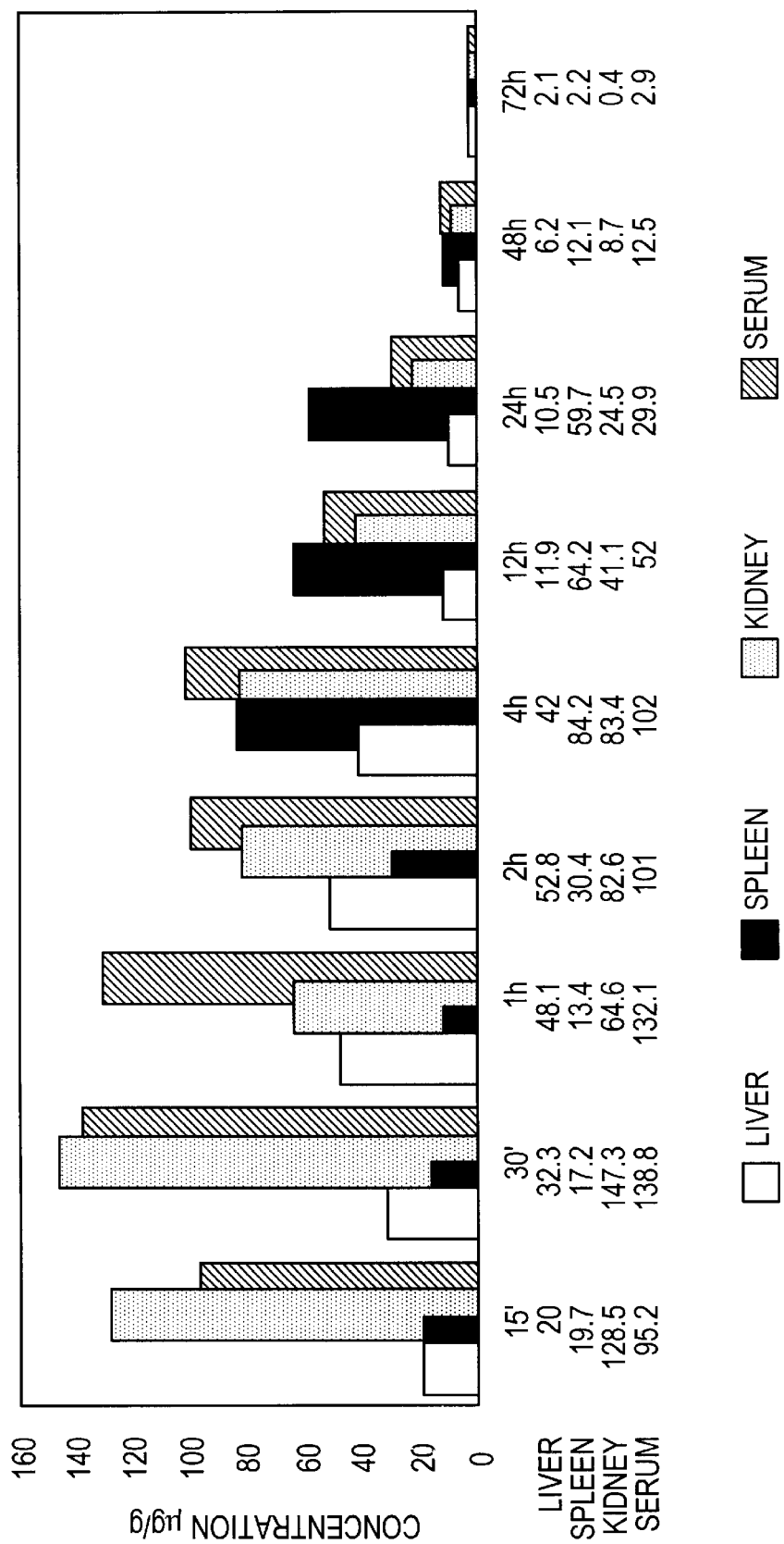
FIGS. 5 and 6 show comparisons of the areas under the curve for carboplantin/liposomally encapsulated carboplatin.
Figure 6:
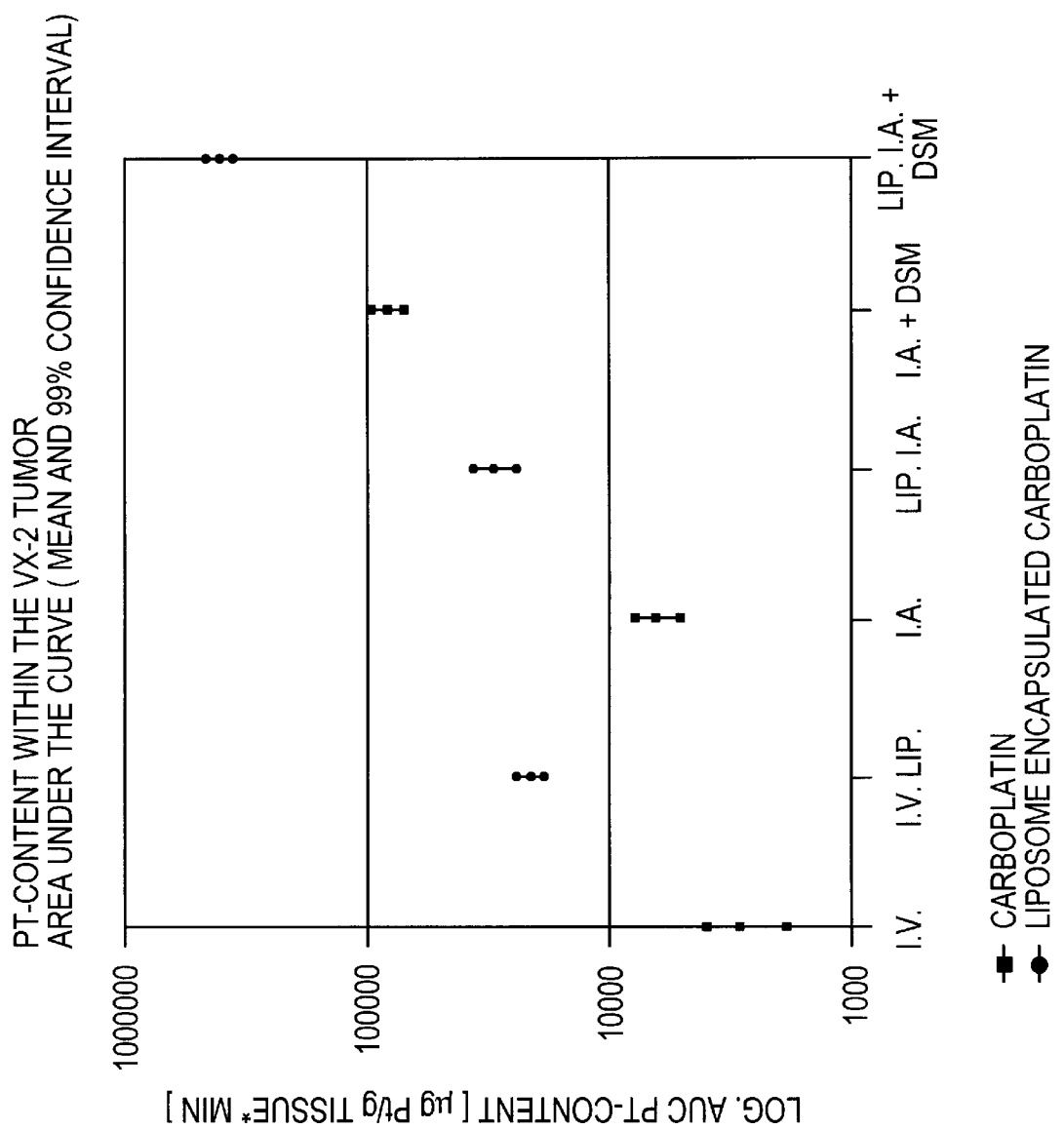
Figure 7:
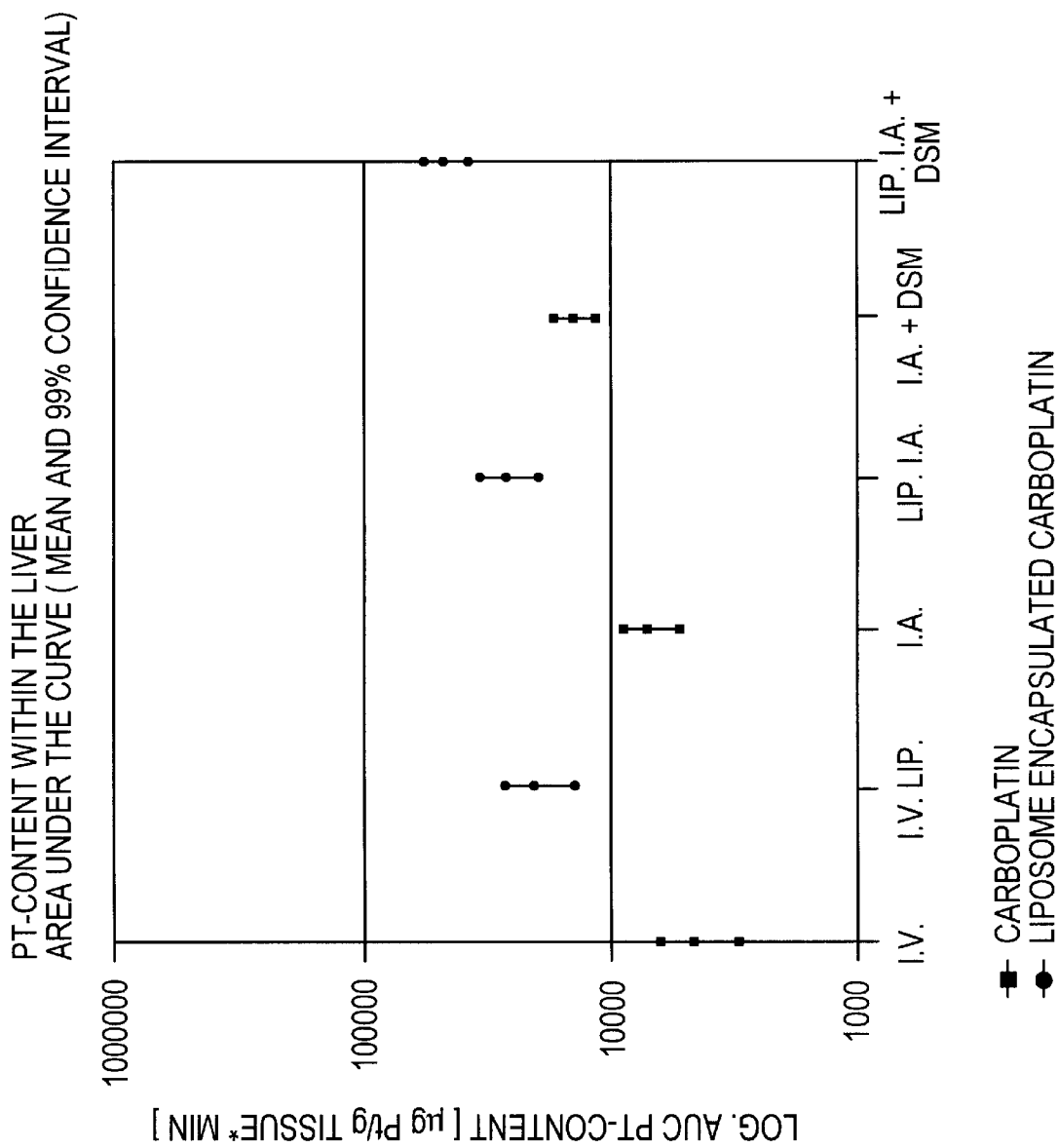
FIG. 7 shows animal experiments.
Figure 9:
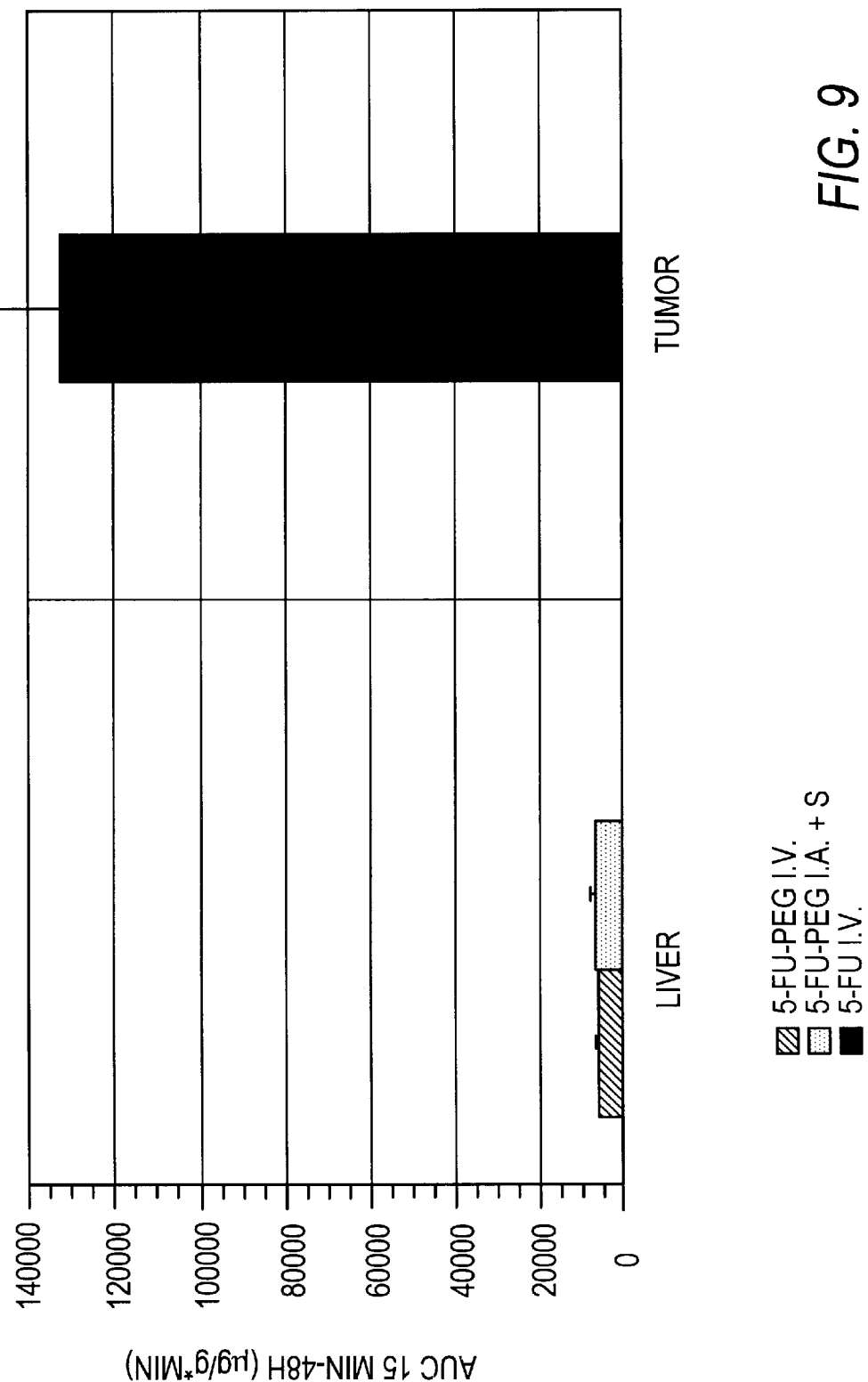
FIGS. 9 to 11 show pharnacokinetics and concentrations with different forms of administration.
Figure 10:
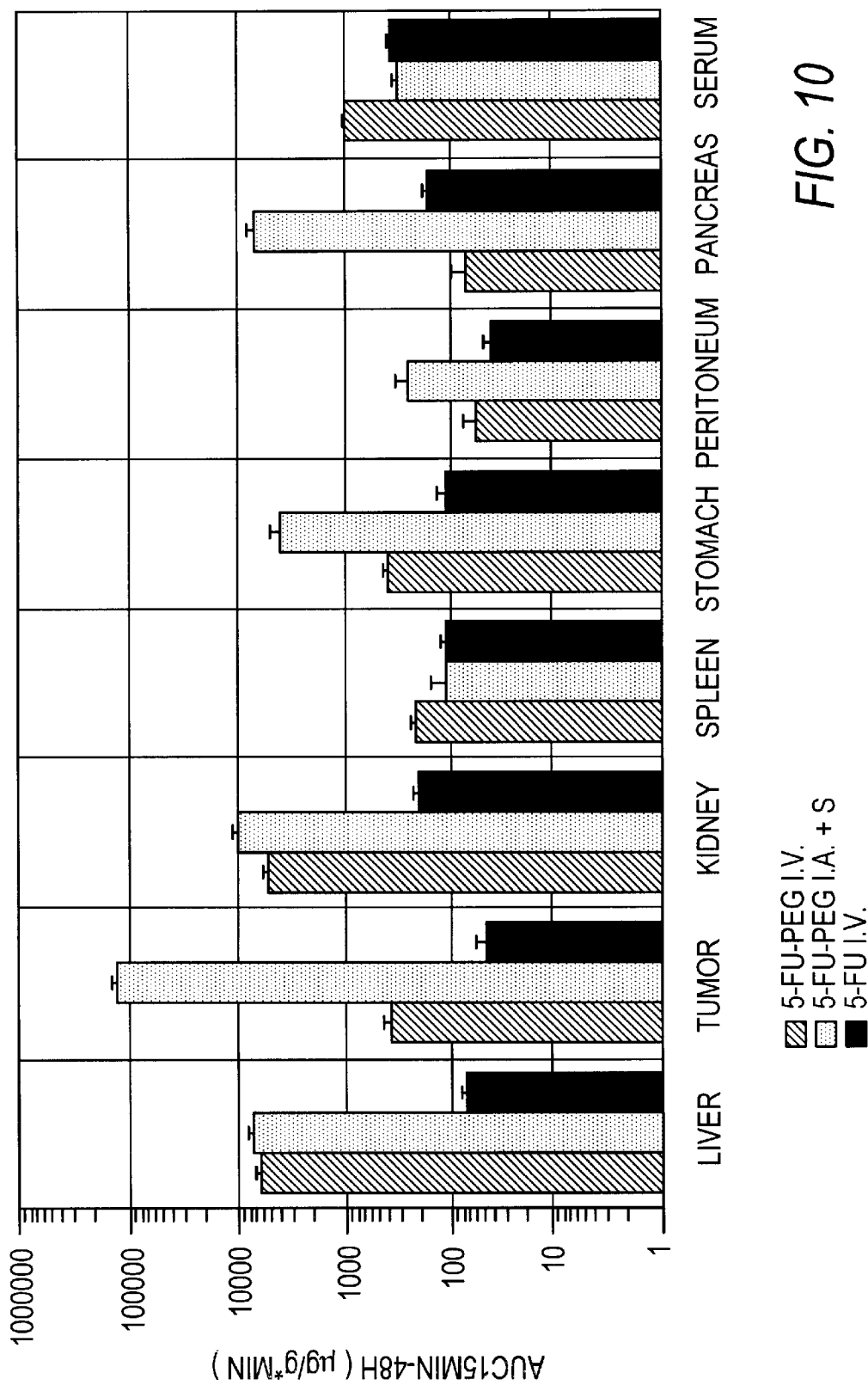
Figure 11:
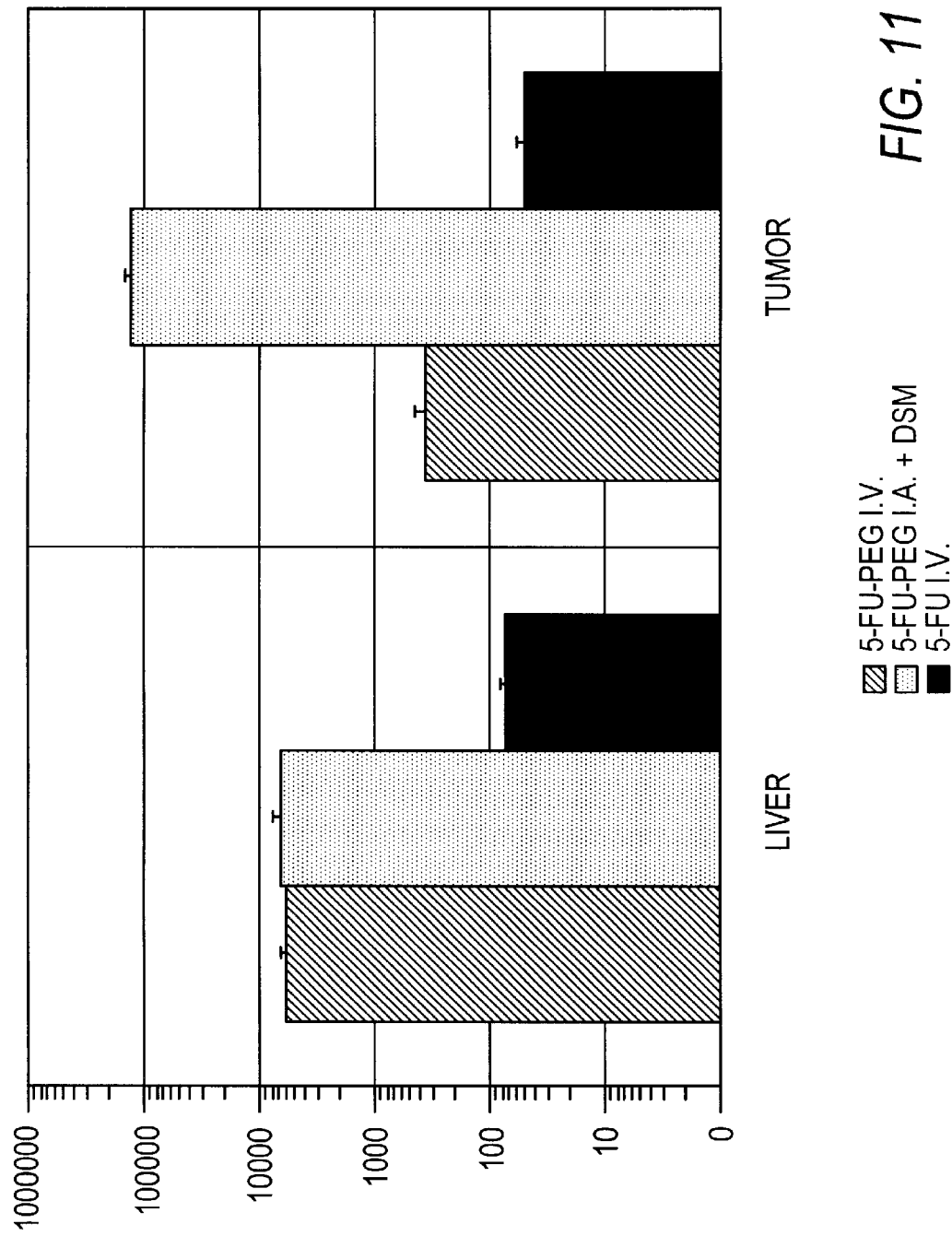

The pharmacokinetics of carboplatin in locoregional applications involved e.g. 50 mg carboplatin with 60 mg DSM, compared to 50 mg SUV-PEG, carboplatin+DSM, as shown in FIGS. 1–3.

The encapsulation of the cytostatic drugs and/or of their metabolites, which are used, suitably with PEG-liposomes, is an important component of the invention. Furthermore, the use of degradable starch particles, which leads to a flow retardation and, with that, increases the contact time, is of great importance.

The cytostatic drugs or their metabolites are encapsulated by procedures known by themselves, in small unilamellar vesicles (SUV)-PEG, large unilamellar vesicles (LUV)-PEG, reversed face evaporation vesicles (RFE)-PEG, multilayer vesicles (MLV)-PEG, or anti-Ki-67 immuno PEG liposomes, or anti-CEA PEG liposomes. For example, such as the preparation of a mixture of egg phosphatidyl choline, cholesterol, dicetyl phosphate and additionally polyethylene glycol in chloroform and diisopropyl ether.

The steroid suitably has the formula (II)

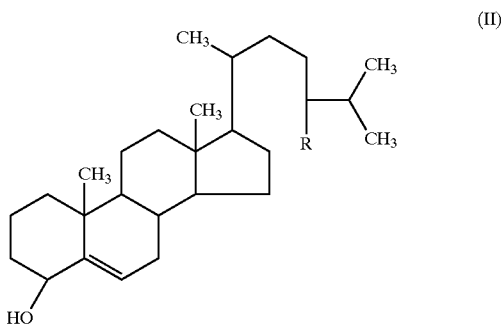

in which R=H (cholesterol), or R=$CH_2$—$CH_2$—O—$CH_2$—$CH_2$—OH (dicholesterol).

The charged lipid component is suitably the anion of diacetyl phosphate, palmitic acid, stearic acid, the anion of a phospholipid such as phosphatidyl tidyl serine, phosphatid acid, or the anion of a sphingolipid such as sulfatid, or polyethylene glycol such as MPES-DSPE.

The molar ratio of the components a:b:c within the first ingredient is suitably 1:0.3:0.1 to 1:1:0.1 or to 1:1:0.5; and the molar ratio of the components c:d is suitably 2:1 to 10:1.

The advantages of the new preparation become evident upon use. Compared to known preparations, the advantages include a significantly higher effectiveness which is a result of the fact that a larger amount of the cytostatic drug can be brought into the tumor and remains there for a longer time. Of decisive importance for the therapeutic effect is the so-called AUC value ("area under the curve"), which sums the residence time and the amount of the therapeutic drug in the tumor. This value is significantly higher when the preparation of the present invention is used, rather than when known preparations, such as the preparation of German patent No. 4,341,478, are used. It is evident, for example from FIG. 12 that the AUC of encapsulated 5-fluorouridine is approximately 417 times as high as that of the free compound, and 4.4 times as high, when degradable starch particles are added.

The following Table summarizes results obtained using carboplatin as the cytostatic drug encapsulated in SUV-PEG and Spherex gelatin foam as the starch particle.

TABLE

| Treatment form | Tumor growth by a factor of (7 days after treatment) | Surging of contrasting agent in the liver |
|---|---|---|
| Control | 3.65 ± 2.45 | unchanged |
| Spherex | 2.38 ± 1.35 | 16% |
| Gelatin foam | 3.93 ± 1.66 | unchanged |
| Carboplatin | 1.45 ± 0.96 | ↓ 7% |
| Carboplatin/ Spherex | 1.15 ± 0.24 | ↓ 19% |
| Carboplatin/ gelatin foam | 0.85 ± 0.08 | ↓ 11% |

The administration regimen of the preparation of the present invention is also of importance. Intraarterial administration generally results in a great increase in the AUC. A further advantage that is important for practical applicability is that the preparation can also be administered orally.

The invention is described in greater detail by the following two examples.

EXAMPLE 1

Vital VX2 tumor cells ($1 \times 10^7$) are implanted in the left lobe of the liver of male chinchilla rabbits. At the same time a port system is implanted in the A. gastroduodenalis.

When the tumor was shown to have reached a size of 2 cm, the animals received, according to a fixed schedule, either the therapeutic drug of the present invention or a mixture of equal doses of the conventional, commercial form as a hepatic intravenous artery infusion (HAI) over the port system. In each case, this contained 60 mg of degradable starch microspheres (Spherex), 50 mg of liposomally encapsulated carboplatin and 5 ml of a 300 mg/ml iodine-containing contrasting agent (Ultravist 300, Schering). At the fixed times (15, 30, 60, 120, 240 minutes, 8 hours, 24 hours, 48 hours), the animals were killed and the concentration of cytostatic drugs in the tumor, liver, spleen, kidneys, pancreas, stomach and lymph nodes was analytically determined by using atomic absorption spectroscopy. The AUC for the liposomal carboplatin was increased 20 fold in the tumor.

EXAMPLE 2

The procedure was the same as in Example 1. However, the CC 531 adenocarcinoma, implanted in the liver of WAG/Rij rats, were treated with the therapeutic drug of the present invention. In this model, the animals were treated with 6 mg of Spherex, 10 mg of liposomal 5-FU and 0.5 ml of Ultravist. At the times prescribed above, the animals were killed and the concentration of 5-FU and its metabolites was determined analytically using HPLC. The AUC for the liposomal 5-FU was increased 20-fold in the tumor. The administration of the newly developed preparation could be observed without any problems directly under X-ray control. The gradual saturation of the vascular bed of the tumor, from the periphery up to the vascular trunk, is portrayed by still pictures over the whole phase of the embolization and could be reconstructed during the whole of the duration of the vascular occlusion as a still picture. It was also possible to document the reperfusion that set in.

What is claimed is:

1. A composition for the treatment of tumors, which comprises
    (a) at least one cytostatic drug component in a PEG-, immuno-, or immuno/PEG liposome, together with
    (b) an embolizing agent of at least one of
        (i) starch particles or degradable starch particles lyophilized from a solution of starch, whereby the solution has a concentration of about 5 mg/ml to 70 mg/ml, wherein said particle range in size from 40 μm to 90 μm and are suspended in a physiological salt solution,
        (ii) gelatine, or
        (iii) nanoparticle, and
    (c) a contrasting agent containing at least one of iodine, gadolinium, and magnetite.

2. The composition of claim 1, wherein the cytostatic drug is encapsulated in SUV-PEG, LUV-PEG, REV-PEG, MLV-PEG, anti-Ki-67 immuno PEG liposome, or anti-CEA PEG liposome.

3. The composition of claim 1 in which the component (a) comprises (a) a natural, semisynthetic, or synthetic amphiphilic compound, (b) a steroid, (c) a charged lipid component, (d) a water- or lipid-soluble cytostatic drug, and (e) a carrier optionally containing one or more additives.

4. The composition of claim 3, wherein the optional additive comprises nanoparticles.

5. The composition of claim 3, wherein said amphiphilic compound is a lipid, surfactant, emulsifier, polyethylene glycol, or lipid PEG.

6. The composition of claim 3, wherein said amphiphillic compound has the formula (I)

$$\begin{array}{c} CH_2-O-R_1 \\ | \\ R_2-O-CH \quad\quad O \\ | \quad\quad\quad || \\ CH_2-O-P-O-CH_2-CH_2-\overset{+}{N}(CH_3)_3 \\ | \\ O^- \end{array}$$

wherein $R_1$ and $R_2$ are independently of each other $C_{10-20}$ alkanoyl, alkenoyl, alkyl, and alkenyl.

7. The composition of claim 3, wherein said steroid has the formula (II)

[steroid structure with R group]

wherein R=H (cholesterol) or $CH_2$—$CH_2$—O—$CH_2$—$CH_2$—OH (diethoxycholesterol).

8. The composition of claim 3, wherein said charged lipid component is the anion of diacetyl phosphate, palmitic acid, stearic acid, the anion of a phospholipid, phosphatid acid, the anion of a sphingolipid, or polyethylene glycol.

9. The composition of claim 8, wherein said charged lipid component is phosphatidyl serine, sulfatid, or MPES-DSPE.

10. The composition of claim 1, wherein said cytostatic drug is carboplatin, 5-fluorouracyl, or 3-fluorouridine.

11. The composition of claim 3, wherein the components (a):(b):(c) are present in a molar ratio of from 0.1:1:1 to 1:1:0.5.

12. The composition of claim 4, wherein the molar ration of the component (c):(d) is from 2:1 to 10:1.

13. The composition of claim 1, wherein the size of said starch particles is from 60 μm to 90 μm.

14. The composition of claim 1, wherein said gelatine is an absorbable gelatine powder.

15. The composition of claim 1, wherein said nanoparticle comprises Poloxamer.

16. The composition of claim 1, wherein said iodine containing contrasting agent comprises a mono- or polyiodated phenyl derivative.

17. The composition of claim 1, wherein said iodine containing contrasting agent comprises Iopromide, Ioxitalamate, Ioxaglate, Iopamidol, Iohexol, Iotralon, Metrizamide, or Ultravist.

18. The composition of claim 3, comprising said cytostatic drug being 5-fluorouracil encapsulated in SUV-PEG, Spherex starch particles, and gadolinium-DTPA contrasting agent.

19. The composition of claim 3, comprising said cytostatic drug being carboplatin encapsulated in SUV-PEG, Spherex or, gel foam starch particles, and Gadolinium-DTPA contrasting agent.

20. A method of treating a tumor, which comprises administering the composition of claim 1 to a patient in need therefor.

21. The method of claim 20, wherein said tumor is a metastasized liver tumor.

22. A method for preparing the composition of claim 1, when said component (b) comprises lyophilized or degradable starch particles, which comprises dissolving from 30 mg to 90 mg starch particles in from 3 ml to 6 ml contrasting agent, and adding thereto a therapeutically effective amount of said cytostatic drug component in said liposome.

* * * * *